(12) United States Patent
Schaeffer et al.

(10) Patent No.: US 8,257,422 B2
(45) Date of Patent: Sep. 4, 2012

(54) OVER-THE-WIRE DETACHMENT MECHANISM

(75) Inventors: Darin G. Schaeffer, Bloomington, IN (US); Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 152 days.

(21) Appl. No.: 12/543,941

(22) Filed: Aug. 19, 2009

(65) Prior Publication Data

US 2011/0046610 A1 Feb. 24, 2011

(51) Int. Cl.
*A61F 2/06* (2006.01)
(52) U.S. Cl. ........................................ 623/1.11
(58) Field of Classification Search .................. 606/108, 606/191, 198, 200, 194; 623/1.11
See application file for complete search history.

(56) References Cited

U.S. PATENT DOCUMENTS

| | | | | |
|---|---|---|---|---|
| 5,250,071 A | 10/1993 | Palermo | | 606/198 |
| 5,925,059 A | 7/1999 | Palermo et al. | | 606/191 |
| 5,944,733 A | 8/1999 | Engelson | | 606/191 |
| 6,214,036 B1 | 4/2001 | Letendre et al. | | 623/1.11 |
| 6,936,058 B2 | 8/2005 | Forde et al. | | 606/200 |
| 7,367,987 B2 * | 5/2008 | Balgobin et al. | | 606/200 |
| 2005/0222537 A1 | 10/2005 | Dinsmoor et al. | | 604/174 |
| 2005/0234505 A1 | 10/2005 | Diaz et al. | | 606/200 |
| 2006/0025801 A1 | 2/2006 | Lulo et al. | | 606/200 |
| 2006/0025802 A1 | 2/2006 | Sowers | | 606/200 |
| 2006/0111771 A1* | 5/2006 | Ton et al. | | 623/1.15 |
| 2006/0276823 A1 | 12/2006 | Mitelberg et al. | | 606/200 |
| 2006/0276829 A1 | 12/2006 | Balgobin et al. | | 606/200 |
| 2007/0073247 A1 | 3/2007 | Ewaschuk | | 604/264 |
| 2008/0097398 A1* | 4/2008 | Mitelberg et al. | | 604/525 |
| 2008/0097462 A1 | 4/2008 | Mitelberg et al. | | 606/108 |
| 2008/0147168 A1 | 6/2008 | Ransbury et al. | | 623/1.15 |
| 2009/0099592 A1 | 4/2009 | Buiser et al. | | 606/200 |

\* cited by examiner

*Primary Examiner* — Ryan Severson
*Assistant Examiner* — Ashley Cronin
(74) *Attorney, Agent, or Firm* — Brinks Hofer Gilson & Lione (57) ABSTRACT

A detachment mechanism, and methods of use, for use in delivering a medical device preferably over a guidewire are provided. The detachment mechanism includes a first and second engagement member. The members are configured to receive the guidewire and have a first end attached to the control member and the device, respectively, a second end, and a notch formed in the body to form an interlocking tooth. The notch is sized to receive the interlocking tooth of the other member. The members are interlockable to couple the medical device to the control member and to allow the guidewire to pass therethrough. The notch can be angled to permit easier detachment between the members and for better torqueability and pushability/pullability between the control member and the medical device. The members can also include a bend region configured to enhance bendability along a portion of the members.

18 Claims, 4 Drawing Sheets

OVER-THE-WIRE DETACHMENT MECHANISM

BACKGROUND

The preferred embodiments of the present invention generally relate to a device for placing a medical device within a body vessel of a body. More particularly, they relate to a detachment mechanism for delivering an implantable medical device over a guidewire to a desired site within a body vessel of a body.

Implantable medical devices are known to be positioned and deployed within body vessels or organs of patients using catheter delivery systems. Treatment with and delivery of such implantable devices are more common nowadays due to the minimally invasive delivery techniques which obviate the need for traditional operational procedures that pose greater risk to patients. Examples of such devices include stents, embolic coils, filters, and vascular occluders.

Some of these devices are conventionally deployed through an introducer catheter after the complete removal of a guidewire. Guidewires generally have a flexible distal portion designed to be advanced across sharp bends at vessel intersections and tortuous vessel paths. For instance, after insertion and translation of the guidewire to a target site, the operator introduces an introducer catheter over the guidewire and advances it to the target site. The guidewire is typically removed, and the operator thereafter introduces the catheter delivery system or a pusher configured to push the medical device through the introducer catheter. The catheter delivery system is advanced through the introducer catheter to the target site, where the medical device is deployed.

Various detachment means for deploying the medical device have been developed in the prior art. Examples of detachment means include the use of a releasable or breakable adhesive bond between the device and pusher, a detachable socket coupling, and a severable connector thread or fiber, among others. Yet, many of these detachment means can only operate the release of a medical device by complete removal of the guidewire which can be time consuming during a medical procedure.

Thus, what is needed is a detachment mechanism for releasing an implantable medical device within a body vessel of a body that can be used without having to remove the entire guidewire.

SUMMARY

A detachment mechanism for use in delivering an implantable medical device having a wire, preferably a guidewire, and using a control member is provided. The control member can include a tubular body such as a biocompatible cannula or a helically wound biocompatible wire forming a tube-like structure. The implantable medical device can include various devices, such as stents, valves, embolic coils, septal occluders, filters, vascular occluders, and/or perfusion devices.

The detachment mechanism includes a first engagement member and a second engagement member. The first engagement member has a body, preferably a tubular body, with a lumen configured to receive the wire. The first engagement member has a proximal end attachable to the control member, a distal end, and at least one notch formed in its body. The notch is disposed proximate the distal end of the first engagement member to define at least one interlocking tooth. The notch can be angled at a first angle relative to the longitudinal axis. The second engagement member has a body, preferably a tubular body, with a lumen configured to receive the wire. The second engagement member has a proximal end, a distal end attachable to the medical device, and at least one notch formed in its body to define at least one interlocking tooth. The notch of the second member can be angled at a second angle relative to the longitudinal axis. The notch can be sized to receive the interlocking tooth of another engagement member such that the first and second engagement members are interlockable to couple the medical device to the control member. When coupled, the lumens of the first and second engagement members are preferably in fluid communication such that the wire is passable therethrough. Typically, the engagement members are oriented so that each notch receives an interlocking tooth of another engagement member.

In one aspect, each of the first and second angles can be an acute angle relative to the longitudinal axis facing either the proximal or distal direction. The first and second angles can be substantially identical. Further, the ends of the engagement members may also be angled at an angle substantially identical to the respective first and second angles. The first and second angles can be an angle in the range of about 30 to about 60 degrees.

In another aspect, each of the first and second engagement members can include a bend region configured to enhance bendability along a portion of the members. The bend region may include a slit disposed at a portion of the body opposite the interlocking tooth. The slit can have a varied cross-sectional area to further enhance bendability in all directions, such as top-to-bottom and/or side-to-side. In another aspect, each of the first and second members may also include a relief portion removed from a portion of the body opposite one of the interlocking tooth, and contiguous with each of the distal end of the first engagement member and the proximal end of the second engagement member.

In another embodiment, a method of deploying an implantable medical device over a guidewire to a treatment site within a body vessel is provided. Preferably, the guidewire is not removed from the body during the deployment procedure. With the control member removably attached to the medical device, the coupled control device and medical device can be introduced over the guidewire. An introducer sheath may have already been advanced over the guidewire, where the sheath can be used to insert the medical device. The first engagement member of the control member is coupled to the second engagement member of the medical device so that the lumens are in fluid communication with each other in order for a distal end of the guidewire to pass therethrough and extend distally past the coupled first and second engagement members. The medical device may then be advanced over the guidewire and positioned at the desirable treatment site. When ready to deploy, the distal end of the guidewire can be retracted in the proximal direction past the coupled first and second engagement members. The second engagement member of the medical device can then be disengaged from the first engagement member of the control member in order to separate the medical device from the control member.

The above, as well as other advantages of the present preferred embodiments, will become readily apparent to those skilled in the art from the following detailed description of a preferred embodiment when considered in the light of the accompanying drawings.

DESCRIPTION OF PREFERRED EMBODIMENTS

In the following discussion, the terms "proximal" and "distal" will be used to describe the opposing axial ends of the inventive device, as well as the axial ends of various component features of the device. The term "proximal" is used in its conventional sense to refer to the end of the device (or component thereof) that is closest to the operator during use of the device. The term "distal" is used in its conventional sense to refer to the end of the device (or component thereof) that is initially inserted into the patient.

Figure 1:
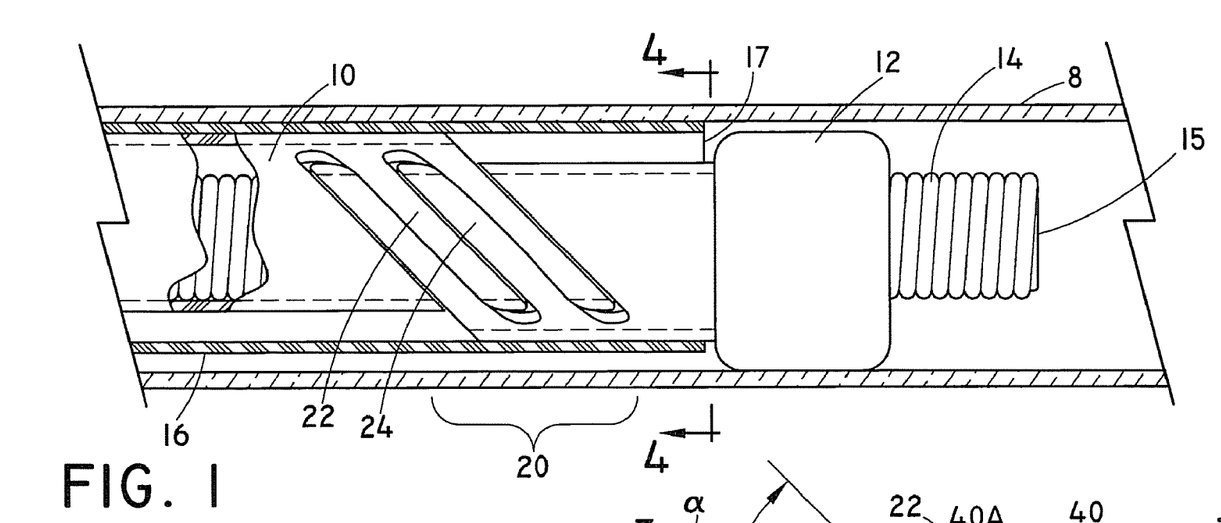
FIG. 1 is a side view of one embodiment of a detachment mechanism.

Referring now to the figures where like reference numerals are used throughout the various views to designate like components, FIG. 1 illustrates a control member 10 coupled to an implantable medical device 12 using one embodiment of a detachment mechanism 20 adapted for movement along a conventional guidewire 14 having a distal end 15. The control member 10, the medical device 12, and the detachment mechanism 20 can be introduced to a body vessel through an introducer sheath 16 having a distal end 17 as shown. The detachment mechanism 20 includes a first engagement member 22 coupled to the control member 10 and a second engagement member 24 coupled to the medical device 12. The control member 10 is configured to slide over the guidewire 14 and to be manipulated external to the patient. For example, the control member 10 can be pushed or pulled along the guidewire 14 and/or rotated around the guidewire. It is to be understood that the detachment mechanism of the present embodiments can be used without a guidewire, an introducer sheath, or both. If used without an inserted guidewire, a control wire sized to fit within the control member can be used in a similar fashion as the guidewire to aid in coupling the engagement members of the detachment mechanism. However, for the purpose of describing the preferred embodiments, reference will be made to only a guidewire, which is also to include other equivalent structures like a control wire.

The control member 10 includes a proximal end that is operable external to the patient and a distal end coupled to the first engagement member 22. The control member and first engagement member may be constructed of two individual components that are assembled or attached by known attachment means, or optionally can be constructed as one piece. Preferably, the control member 10 includes a lumen sized and configured to receive the guidewire 14. Examples of the control member 10 can include a tubular body such as a biocompatible cannula or a helically wound biocompatible wire forming a tube-like structure. One skilled in the art will appreciate that although the control member is shown as generally cylindrical, the control member can have a variety of shapes and configurations, including rectangular, oval, D-shaped, triangular, and/or irregular.

The medical device 12 includes a proximal end that is coupled to the distal end of the second engagement member 24. The medical device and the second engagement member may be constructed of two individual components that are assembled or attached by known attachment means, or optionally can be constructed as one piece. The medical device 12 may include a portion configured to allow the guidewire 14 to pass through, and may be self-expandable. Non-limiting examples of medical devices 12 that can be deployed using the detachment mechanism 20 include stents, valves, embolic coils, septal occluders, filters, vascular occluders, and/or perfusion devices.

The first and second engagement members 22, 24 will now be described in more detail. It is to be understood that, for the purposes of describing both the first and second engagement members, reference will be only made to the first engagement member 22. In preferred embodiments, the second engagement member 24 is identically constructed but oppositely oriented as shown in the figures.

Figure 2:
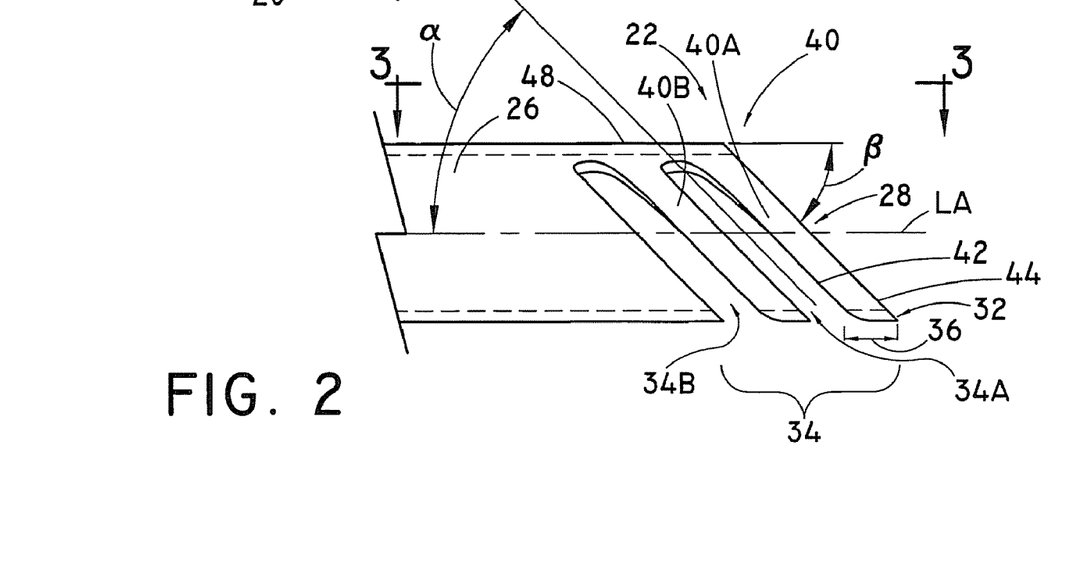
FIG. 2 is a side view of one embodiment of an engagement member of a detachment mechanism.

FIG. 2 shows one illustrative embodiment of the first engagement member 22 including a body 26 having a lumen 28 about a longitudinal axis LA. The lumen 28 is configured and sized to receive a guidewire. Preferably, the body 26 is sized to optimally reduce the cross-sectional area of the body in order to enhance deliverability of the device, while at the same time having a lumen sized to receive the guidewire. One skilled in the art will appreciate that although the body 26 is shown as generally cylindrical, the body can have a variety of shapes and configurations, including rectangular, oval, D-shaped, triangular, and/or irregular. Preferably, the entire body is rounded at its outside surface in order to decrease trauma to the vessel while being used within the vessel and in order to prevent snagging structures along the vessel. The body 26 may be the same size, shape and configuration as the control member, or optionally, the body of the engagement member and the control member may be different from one another. The body 26 may have a proximal end attached to the distal end of the control member 10, a distal end 32, and one or more notches, generally identified as reference numeral 34, formed through the body 26.

The notch 34 is preferably disposed a longitudinal distance 36 from the distal end 32 of the body 26 in order to form an interlocking tooth, generally identified as reference numeral 40. FIG. 2 illustrates a first notch 34B and a second notch 34A distal to the first notch forming a first interlocking tooth 40B and a second interlocking tooth 40A distal to the first interlocking tooth. The notches may be equally spaced from one another by a longitudinal distance equal to distance 36, or the spacing may vary between adjacent notches. If a tubular body is used, the interlocking tooth resembles a ring-like structure.

The notch 34A has a distal side and a proximal side that define the edges of the notch. The sides can be equally angled, resulting in the notch 34A being angled at a first angle α relative to the longitudinal axis. However, only one of the sides of the notch may be angled at the first angle. To this end, the interlocking tooth 40A, which shares its proximal side 42 with the distal side of notch 34A, is then also angled at an angle identical to the first angle α. The first angle α is dimensioned to permit the operator to decouple the first and second engagement members 22, 24 more easily by reducing the potentiality for catching or snagging any blunt edges often associated with conventional devices. The angle α can be any angle suitable to enhance disengagement or engagement of the interlocking teeth and notches. In some embodiments, the angle α can be about 15° to about 75° relative to the longitudinal axis; more preferably, about 30° to about 60°; and most preferably, about 45°. The angle α may be acute facing the proximal direction, as shown in FIG. 2. Optionally, the angle α may be facing the distal direction.

Figure 6A:
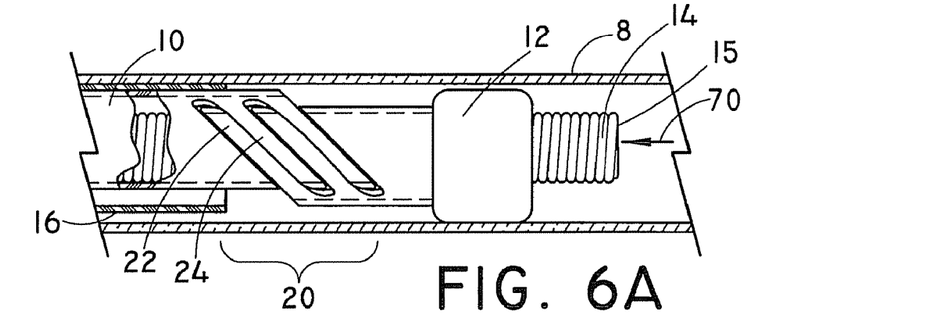
FIGS. 6A-6C illustrate a method of using one embodiment of a detachment mechanism.
Figure 6B:
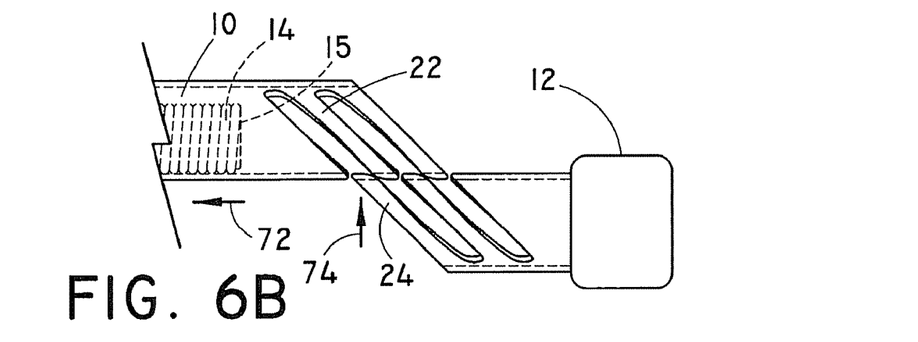

As mentioned previously, the interlocking tooth 40A can also have an angled proximal side 42 for the interlocking tooth of another engagement member to ride against as the first engagement member 22 is being pulled or withdrawn in the proximal direction, as shown in FIG. 6B. The distal end 32 of the engagement member, which coincides with the distal side 44 of the interlocking tooth 40A, may be perpendicular to the longitudinal axis. However, according to FIG. 2, the distal side 44 is preferably angled at an angle β which is substantially identical to the first angle α. Because of the various angled surfaces of the engagement member, force transfer between the control member and the medical device is enhanced when rotating and/or pushing/pulling the control member to position the medical device at the target site.

Figure 2A:
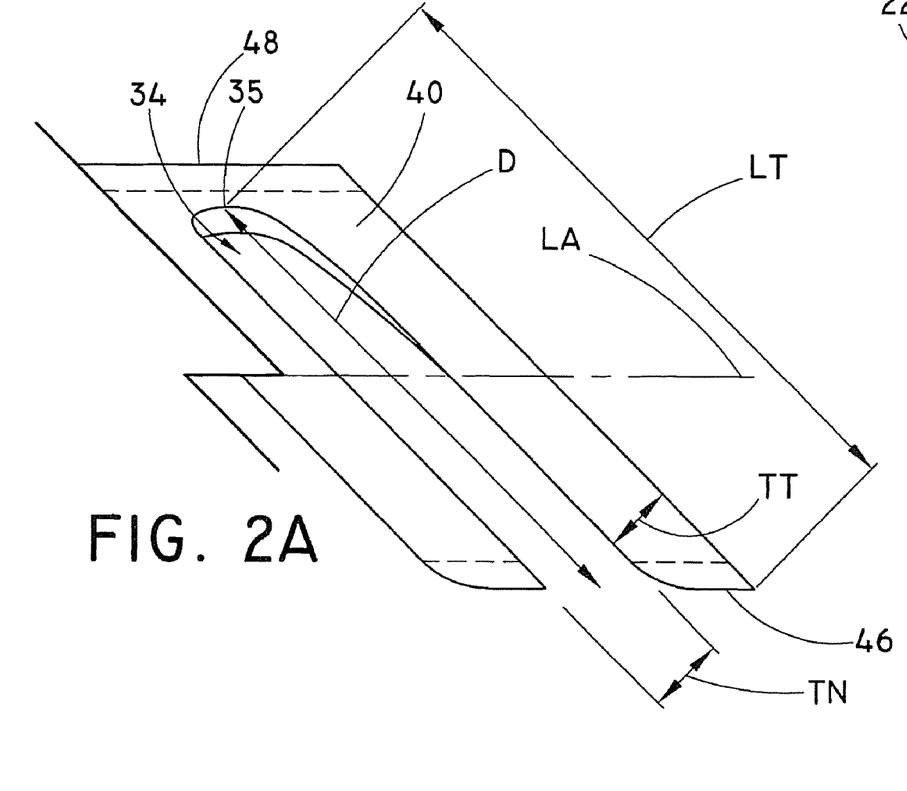
FIG. 2A is a side view of one embodiment of a notch and an interlocking tooth of an engagement member.

FIG. 2A is a detailed view of the notch 34 and the interlocking tooth 40. The notch 34 can be formed by transversely cutting through the body of the engagement member. Preferably, the notch 34 is cut from a first side 46 of the body 26, through the body and past the longitudinal axis to form a spine 48 at a second, opposite side of the body. The depth D of the notch 34 may be dependent on the circumference of the body 26. Removing too much material will weaken the spine 48 to a point where force transferability is diminished, making it difficult to push/pull or rotate the engagement member, while leaving too much material will strengthen the spine to a point where flexibility is lost, making is difficult to navigate through tortuous paths of the body vessel. The width TT and length LT of the interlocking tooth 40 will be dependent on the width TN and depth D of the notch 34 of the other engagement member, respectively. For example, the width TT and length LT of the interlocking tooth 40 is sized to engage the notch of the other engagement member, while the width TN and depth D of the notch 34 is sized to receive the interlocking tooth of the other engagement member. Preferably, the width TN of the notch 34 is about 5% to about 15%, and preferably about 10%, larger than the width of the interlocking tooth of the other engagement member. The depth D of the notch 34 is about 50% to about 90% of the circumference of the engagement member or optionally up to 90% of the diameter of the engagement member. The end 35 of the notch 34 is preferably rounded to further reduce any stress risers that can form when using the device, which can lead to fracturing.

Figure 3:
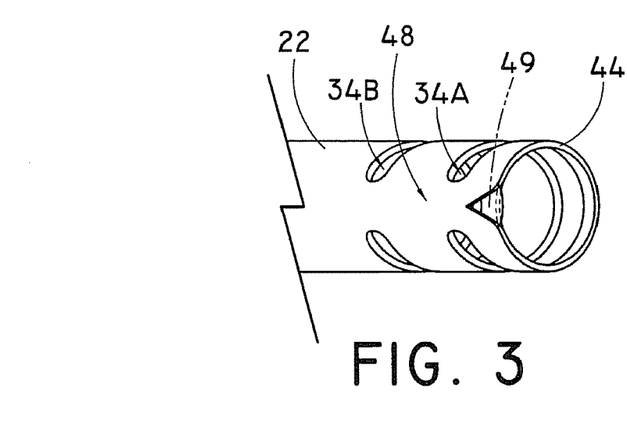
FIG. 3 is a bottom view of a distal end of one embodiment of an engagement member.

FIG. 3 illustrates another embodiment of the detachment mechanism 20 having a portion 49 removed at the distal end from the spine 48. The removed portion can be any of a variety of shapes such as a V-shape, U-shape, square or the like. The removed portion 49 can shorten the spine 48 so that the spine is more flexible for tortuous paths. Additionally, the removed portion 49 can provide additional freedom of movement for the adjacent outer surface of the other engagement member to move without any contact, or little contact, with the removed portion 49 during movement through a tortuous path.

Figure 4:
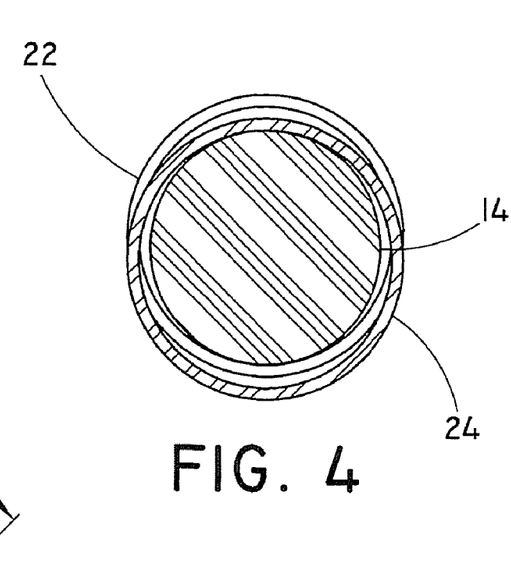
FIG. 4 is a cross-sectional view of the detachment mechanism taken along lines 4-4 of FIG. 1.

FIG. 4 is a cross-sectional view of the coupled first and second engagement members 22, 24 of FIG. 1. The proximity of the guidewire 14 is shown with respect to the first and second engagement members 22, 24. Preferably, the cross-sectional area of the lumens of the engagement members 22, 24 is sized to receive the guidewire 14 and to minimize the overall cross-sectional area of the coupled engagement members 22, 24.

Figure 5:
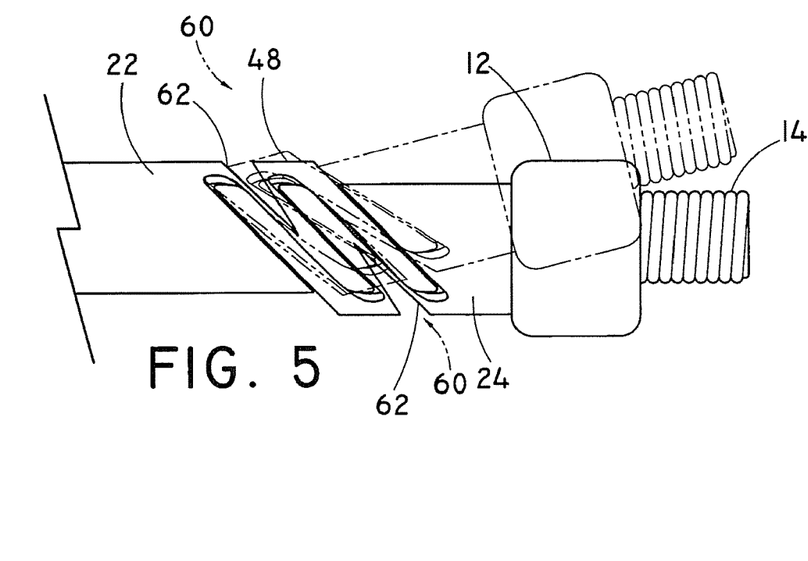
FIG. 5 is a side view of one embodiment of a detachment mechanism with a bend region.
Figure 5A:
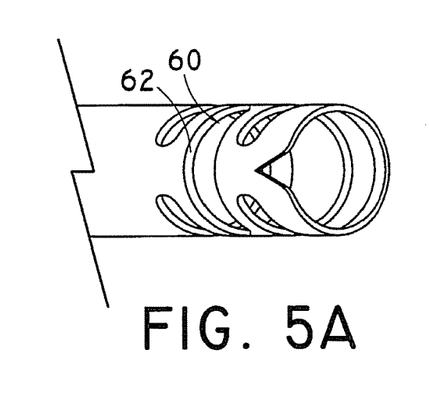
FIG. 5A is a bottom view of one embodiment of a detachment mechanism depicting a bend region.

FIGS. 5 and 5A depicts another embodiment of the detachment mechanism 20 having a bend region 60. The bend region 60 is configured to allow greater flexibility in the engagement member while being translated through a tortuous path of the body vessel. The bend region 60 can include one or more perforations or one or more relief cuts, each partially or fully formed in the wall of the body of the engagement member. In one embodiment, the bend region 60 includes a relief cut 62 formed in the wall of the body 26 at the spine 48, preferably opposite one of the interlocking teeth. The relief cut 62 can have any of several shapes and sizes. For example, the relief cut 62 shown in FIG. 5A is an oblong slit that has more material removed at the middle than at the ends of the slit. Further, the relief cut 62 is shown in the FIG. 5 to extend about 50% of the circumference of the engagement member body, but can extend up to about 80% or more of the circumference of the engagement member body. At the higher extension percentages, the relief cut can not only provide greater flexibility along the spine 48, but also greater flexibility from side-to-side transverse to the spine.

Figure 6C:
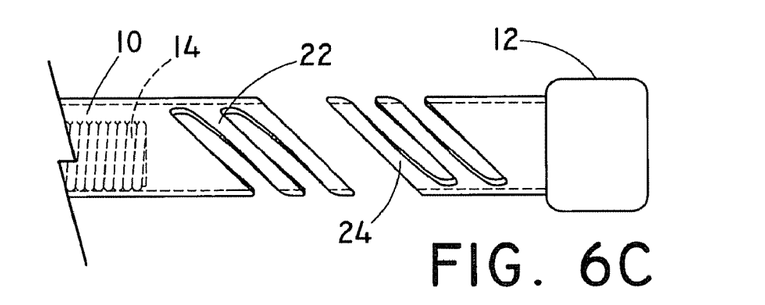

Reference will now be made to FIGS. 6A-6C to describe the operability of one embodiment of the detachment mechanism 20 to deliver the medical device 12 within a body vessel 8 or organ. The guidewire 14 is inserted and translated to a treatment site using conventional techniques. Further, the introducer sheath 16 can be then inserted over the guidewire 14 and the distal end 17 of the sheath is likewise translated to the treatment site. Conventional interventional radiography can be used to ensure the exact locations of the distal end 15 of the guidewire 14 and the distal end 17 of the introducer sheath 16.

The medical device 12 and the control member 10 are coupled using the detachment mechanism 20. The coupled medical device 12 and the control member 10 are inserted over the guidewire 14, and within the introducer sheath 16, such that the respective lumens of the first and second engagement members 22, 24 of the detachment mechanism 20 receive the guidewire. The control member 10 is used to navigate the medical device 12 through the body vessel by being translated over the guidewire and through the sheath to the desired treatment site. Once at the treatment site, the sheath may be partially withdrawn while in the body vessel, as shown in FIG. 6A, or completely withdrawn from the body. To this end, the medical device 12 is preferably implanted at the treatment site or otherwise sufficiently affixed so that when control member 10 is retracted the medical device does not move, or has minimal movement, from the treatment site.

In alternative embodiments, the coupled medical device and control member are inserted only over the guidewire without the use of an introducer sheath. In other alternative embodiments, a guidewire is not used and the sheath is navigated through the body vessel and placed at the treatment site. Here, the medical device and the control member are coupled together with a control wire that can be suitably released with the use of a control unit that is located external to the patient. The control wire may have a portion removably attached to the engagement members in a suitable manner to couple the engagement members. Optionally, a separate loop may couple the engagement members, and a portion of the loop can be removably attached to the control wire. The control wire can extend through the lumen of the control member 10 all the way through the proximal end of the delivery system or configured to only extend through the region where the lumens are in communication. The coupled medical device and control member can then be inserted through the vessel, preferably through an introducer sheath, to the treatment site. The control wire can then be released from the lumens in order to deploy the device.

According to FIG. 6A, the guidewire 14 is retracted in the proximal direction, represented by arrow 70, such that the distal end 15 of the guidewire is proximal to the coupled engagement members 22, 24, as shown in FIG. 6B.

According to FIG. 6B, the control member can be withdrawn in the proximal direction, represented by arrow 72, such that sides of the interlocking teeth of the first engagement member 22 ride along the sides of the interlocking teeth of the second engagement member 24. Because the medical device is relatively affixed at the treatment site, the first engagement member 22 is lifted, represented by arrow 74, during withdrawal of the control member without catching on any portions of the second engagement member 24. Although not shown, the control member 10 can be rotated, singly or in combination with the proximal withdrawal thereof, with respect to the medical device such that the engagement members decouple.

According to FIG. 6C, the first engagement member 22 will become decoupled from the second engagement member 24, leaving the medical device deployed at the treatment site. Thereafter, the control member 10 can be completely removed from the body vessel, along with the guidewire 14 and introducer sheath 16.

Leaving the guidewire within the sheath can be advantageous in situations, where there is a higher risk of the sheath moving during advancement of the medical device. One situation is at branched body vessel section where a portion of a sheath is positioned with the branch vessel. When retracting the guidewire partially away from the branch vessel, there is a higher risk that the sheath can move away from the branch vessel or reposition in the main vessel during advancement of the medical device through the sheath. With use of the detachment mechanism, the clinician would only need to retract the sheath partially and reposition the guidewire to the treatment site so that the sheath can again be placed at the treatment site. Otherwise, the doctor would have to reinsert the guidewire all the way through the body vessel, reposition the sheath, remove the guidewire, and readvance the medical device through the sheath.

Figure 7:
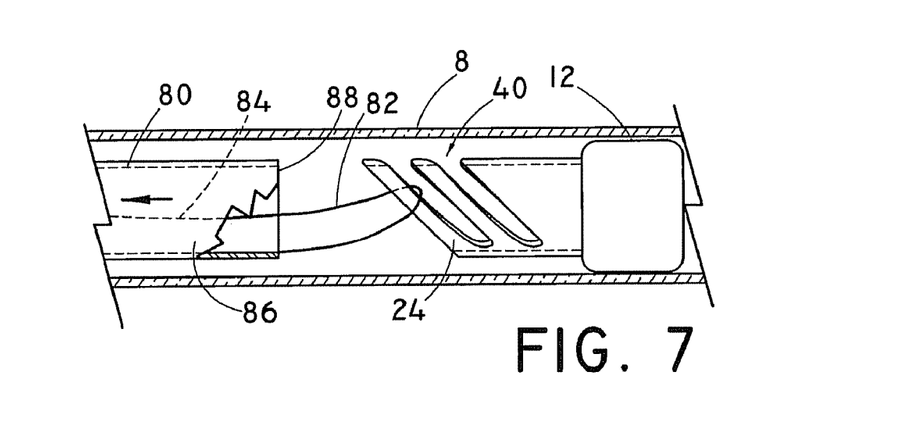
FIG. 7 illustrates a method of retrieving a medical device.

With reference to FIG. 7, once implanted, the medical device 12 may be retrieved from the vessel 8 by use of a snare device 80 or other standard percutaneous retrieval devices. Accordingly, the adaptations identified herein should not be construed in any way as limiting deployment and removal means. One example of a snare device is described in U.S. Pat. No. 5,697,936, which is hereby incorporated by reference in its entirety. The snare device 80 can be configured as a single wire loop 82 affixed to a draw means 84 contained in and extending through a tube 86. The tube 86 includes a distal end 88 against which the loop 82 abuts, and the wire loop 82 is closed by moving the draw means 84 in a direction outward of the body. The wire loop 82 is preferably affixed to the tube 86 at its distal end 88. This affirmatively prevents withdrawal of the wire loop 82 into the tube 86 and ensures that the engagement of the wire loop 82 with one of the interlocking teeth 40 of the engagement member 24. Once tightened around the interlocking tooth 40, the medical device 12 can be withdrawn through the vessel. Preferably, the snare is used with a sheath, where the device can collapse within the sheath as the draw means 84 is pulled. In such instance, the sheath containing the medical device can be withdrawn from the vessel. Referring back to FIG. 2, having the angle α face the distal direction, rather than the proximal direction as shown, may enhance snareability of the interlocking tooth with the snare device 80.

In one example of making the engagement member, a cannula of Nitinol having 0.8 mm outer diameter and 0.1 mm wall thickness is placed and removably attached to a mandrel. After suitable preparations are made for laser cutting, portions of the cannula are cut to define at least one of the following: one or more notches, the angle of distal end, the removed portion from the distal end, and the relief cut from the spine. After laser cutting, the cannula can be polished, for example by electropolishing, heat treated, and otherwise prepared for attachment to a control member and/or an implantable medical device for use within a body vessel. In one preferred embodiment, the depth D of the notch is approximately 90% the outer diameter of the cannula; the width TN of the notch is approximately 10% larger than the width TT of the interlocking tooth; and the angle of the notch is approximately 45 degrees.

One of the advantages of the detachment mechanism is that the engagement members are configured such that they can easily interlock and disengage. Another feature is that the members can easily slide over a guidewire and/or optionally through an introducer sheath in order to deliver a medical device to a treatment site. Another feature is the improved pullability/pushability and torqueability transferred from the control member to the medical device via the detachment mechanism, which enhances operator control during delivery.

In accordance with the provisions of the patent statutes, the present invention has been described in what is considered to represent its preferred embodiment. However, it should be noted that the invention can be practiced otherwise than as specifically illustrated and described. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

The invention claimed is:

1. A detachment mechanism for use in delivering a medical device using a control member over a guidewire comprising:
a first engagement member including a tubular body having a lumen about a longitudinal axis and configured to receive said guidewire, the first engagement member having a proximal end attached to said control member, a distal end, and at least two notches formed in the tubular body of the first engagement member proximate the distal end thereof to define at least two interlocking teeth having ring-like structures, the notches of the first engagement member being angled at a first acute angle through the tubular body relative to the longitudinal axis; and
a second engagement member including a tubular body having a lumen about a longitudinal axis and configured to receive said guidewire, the second engagement member having a proximal end, a distal end attached to said medical device, and at least two notches formed in the tubular body of the second engagement member to define at least two interlocking teeth having ring-like structures, the notches of the second engagement member being angled at a second acute angle through the tubular body relative to the longitudinal axis,
wherein the notches of each of the first and second engagement members is sized to receive the interlocking teeth of the other of the first and second engagement members such that the first and second members are interlockable to couple said control member to said medical device disposed distal thereto, wherein, when coupled, the lumens of the first and second engagement members are in communication with one another such that said guidewire is passable therethrough.

2. The detachment mechanism of claim 1, wherein each of the first and the second angles further comprises an acute angle facing in a proximal direction.

3. The detachment mechanism of claim 1, wherein each of the first and the second angles further comprises an acute angle facing in a distal direction.

4. The detachment mechanism of claim 1, wherein the first and second angles are in a range of about 30 to about 60 degrees.

5. The detachment mechanism of claim 1, wherein at least one of the first and second engagement members further comprises a bend region configured to facilitate bending of said engagement member.

6. The detachment mechanism of claim 5, wherein the bend region comprise a slit disposed at a portion of the body opposite the interlocking teeth, the slit comprising a middle region interposed between ends, wherein the middle region of the slit is larger than at the ends to form an oblong shape.

7. The detachment mechanism of claim 1, wherein each of the distal end of the first engagement member and the proximal end of the second engagement member is angled at an acute angle substantially identical to the respective first and second angles.

8. The detachment mechanism of claim 1, wherein each of the first and second engagement members further comprises a relief portion removed from a portion of the body opposite the interlocking teeth, the removed relief portion formed contiguous with each of the distal end of the first engagement member and the proximal end of the second engagement member.

9. The detachment mechanism of claim 1, wherein the notches of each of the first and second engagement members further comprises a rounded end adapted to reduce stress risers.

10. The detachment mechanism of claim 1, wherein each of the notches of the first engagement member extends circumferentially around a majority of the tubular body with the center of the notches disposed distal from ends of the notches, each of the interlocking teeth of the first engagement member being disposed distal from one of the notches and extending circumferentially around a majority of the tubular body with the center of the interlocking teeth disposed distal from ends of the interlocking teeth, and each of the notches of the second engagement member extends circumferentially around a majority of the tubular body with the center of the notches disposed proximal from ends of the notches, the interlocking teeth of the second engagement member being disposed proximal from one of the notches and extending circumferentially around a majority of the tubular body with the center of the interlocking teeth disposed proximal from ends of the interlocking teeth.

11. A detachment mechanism for use in delivering a medical device using a control member comprising:
a first engagement member and a second engagement member each including a tubular body having a lumen about a longitudinal axis configured to receive a wire, each of the first and second engagement members having a first end connected to said respective control member and medical device, a second, opposite end, and at least two notches formed in the tubular body proximate the second end thereof to form at least two interlocking teeth having ring-like structures,
the two notches of the engagement members being sized to receive the interlocking teeth of the other engagement member, wherein the first and second engagement members are interlockable to couple said medical device to said control member, wherein when coupled the lumens of each of the first and second members are in communication such that said wire is passable therethrough,
wherein each of the first and second engagement members includes a bend region configured to enhance bendability along a portion opposite the interlocking teeth of the first and second engagement members.

12. The detachment mechanism of claim 11, wherein the notches further comprise a first notch and a second notch to form a first interlocking tooth having a ring-like structure and a second interlocking tooth having a ring-like structure proximal to the first interlocking tooth.

13. The detachment mechanism of claim 12, wherein the bend region is disposed at a portion of the body opposite the second interlocking tooth.

14. The detachment mechanism of claim 12, wherein the body of each of the first and second engagement members further comprises a relief portion removed from a portion of the body opposite the first interlocking tooth and contiguous with the second end of the engagement member.

15. The detachment mechanism of claim 12, wherein each of the first and second notches is angled at an acute angle relative to the longitudinal axis.

16. The detachment mechanism of claim 15, wherein the second end of each of the first and second engagement members is angled at an acute angle substantially identical to the acute angle of the notches.

17. The detachment mechanism of claim 11, wherein the notches have a width of up to about 10% larger than a width of the interlocking teeth, and a depth in a range of between about 50% to about 90% of an outer diameter of the engagement member.

18. The detachment mechanism of claim 11, wherein each of the notches of the first engagement member extends circumferentially around a majority of the tubular body with the center of the notches disposed distal from ends of the notches, each of the interlocking teeth of the first engagement member being disposed distal from one of the notches and extending circumferentially around a majority of the tubular body with the center of the interlocking teeth disposed distal from ends of the interlocking teeth, and each of the notches of the second engagement member extends circumferentially around a majority of the tubular body with the center of the notches disposed proximal from ends of the notches, the interlocking teeth of the second engagement member being disposed proximal from one of the notches and extending circumferentially around a majority of the tubular body with the center of the interlocking teeth disposed proximal from ends of the interlocking teeth.

* * * * *

UNITED STATES PATENT AND TRADEMARK OFFICE
CERTIFICATE OF CORRECTION

PATENT NO. : 8,257,422 B2
APPLICATION NO. : 12/543941
DATED : September 4, 2012
INVENTOR(S) : Darin G. Schaeffer et al.

Page 1 of 1

It is certified that error appears in the above-identified patent and that said Letters Patent is hereby corrected as shown below:

In the Claims

In column 8, claim 1, line 62, before "sized to receive the" replace "is" with --are--.

In column 9, claim 6, line 17, before "a slit disposed" replace "comprise" with --comprises--.

In column 9, claim 9, line 35, before "a rounded end adapted" replace "comprises" with --comprise--.

Signed and Sealed this
Fifth Day of February, 2013

Teresa Stanek Rea
*Acting Director of the United States Patent and Trademark Office*